United States Patent
Hagiya

(10) Patent No.: US 7,993,614 B2
(45) Date of Patent: Aug. 9, 2011

(54) METHOD FOR RECOVERING TUNGSTEN

(75) Inventor: Koji Hagiya, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/067,336

(22) PCT Filed: Sep. 20, 2006

(86) PCT No.: PCT/JP2006/319091
§ 371 (c)(1),
(2), (4) Date: Mar. 19, 2008

(87) PCT Pub. No.: WO2007/034972
PCT Pub. Date: Mar. 29, 2007

(65) Prior Publication Data
US 2009/0148362 A1    Jun. 11, 2009

(30) Foreign Application Priority Data

Sep. 21, 2005  (JP) .................................. 2005-273385

(51) Int. Cl.
*C01G 37/00* (2006.01)

(52) U.S. Cl. ......................................... 423/55; 423/53
(58) Field of Classification Search ...................... 423/55
See application file for complete search history.

(56) References Cited

U.S. PATENT DOCUMENTS 7,425,519 B2 * 9/2008 Yonehara et al. ............. 502/150
2002/0025906 A1   2/2002 Hagiya et al.

FOREIGN PATENT DOCUMENTS

| DE | 4002014 A * | 8/1990 |
| EP | 1 748 042 A1 | 1/2007 |
| GB | 894592 A | 4/1962 |
| JP | 46-41526 B | 12/1971 |
| JP | 55-4459 B2 | 1/1980 |
| JP | 55-51439 A | 4/1980 |
| JP | 62-174038 A | 7/1987 |
| JP | 02-217321 A | 8/1990 |
| JP | 08-002920 A | 1/1996 |
| JP | 8-291104 A | 11/1996 |
| JP | 2002-201147 A | 7/2002 |

OTHER PUBLICATIONS

Extended EP Search Report issued Oct. 25, 2010 from the EP Patent Office in counterpart EP Application No. 06 79 8349.4.
English translation of CN Office Action issued Sep. 9, 2010 in counterpart CN Application No. 200680034562.1.

* cited by examiner

*Primary Examiner* — Melvin C Mayes
*Assistant Examiner* — Melissa Stalder
(74) *Attorney, Agent, or Firm* — Panitch Schwarze Belisario & Nadel LLP

(57) ABSTRACT

A method for recovering tungsten from a reaction mixture obtained by reacting an organic compound with hydrogen peroxide in the presence of a tungsten catalyst comprising blowing a gas into the reaction mixture to precipitate tungstic acid ($WO_3 \cdot H_2O$) and separating tungstic acid precipitated.

7 Claims, No Drawings

US 7,993,614 B2

METHOD FOR RECOVERING TUNGSTEN

CROSS-REFERENCE TO RELATED APPLICATION

This application is a section 371 of International Application No. PCT/JP2006/319091, filed Sep. 20, 2006, which was published in the Japanese language on Mar. 29, 2007 under International Publication No. WO 2007/034972 A1 and the disclosure of which is incorporated herein by reference.

TECHNICAL FIELD

The present invention relates to a method for recovering tungsten.

BACKGROUND ART

A tungsten catalyst is used as a catalyst for various oxidation reactions using hydrogen peroxide as an oxidizing agent. The oxidation reactions are usually conducted in the presence of water, and the tungsten catalyst used is dissolved in a reaction mixture. Therefore, various methods for recovering tungsten contained in the tungsten catalyst used from the reaction mixture are reported.

For example, JP 8-291104 A and JP 55-4459 B disclose methods for recovering tungstic acid by contacting an oxidation reaction mixture with an ion-exchanged resin. JP 46-41526 B discloses a method comprising precipitating tungsten catalyst by adding acetone, tetrahydrofuran, dioxane, n-propanol or isopropanol in an amount of eight times by weight or more to an oxidation reaction mixture and recovering it. WO 2005/110962 A discloses a method comprising cooling the reaction mixture obtained by reacting wastewater which contains hydroxycaproic acid and which is discharged from the oxidation reaction of cyclohexane with hydrogen peroxide in the presence of a tungsten catalyst and isolating solids of tungstic acid precipitated.

DISCLOSURE OF THE INVENTION

The present invention provides a method for recovering tungsten from a reaction mixture obtained by reacting an organic compound with hydrogen peroxide in the presence of a tungsten catalyst comprising blowing a gas into the reaction mixture to precipitate tungstic acid ($WO_3.H_2O$) and separating tungstic acid precipitated.

BEST MODE FOR CARRYING OUT THE PRESENT INVENTION

Examples of the tungsten catalyst include tungstens such as tungsten metal, tungsten boride, tungsten carbide, tungsten sulfide, tungsten oxide, tungstic acid and a salt of tungstic acid; and an oxide of tungsten obtained by reacting at least one tungstens with hydrogen peroxide.

Examples of the salt of tungstic acid include an alkali metal tungstate such as sodium tungstate and potassium tungstate, an alkaline earth metal tungstate such as calcium tungstate and magnesium tungstate, and ammonium tungstate.

As tungstens, commercially available one is usually used. As tungstic acid, one prepared by reacting the above-mentioned salt of tungstic acid with an acid such as sulfuric acid may be used. As the salt of tungstic acid, one prepared by reacting tungstic acid with the corresponding base may be used.

Among thus tungsten catalysts, tungstic acid, the salt of tungstic acid and the oxide of tungsten obtained by reacting at least one tungstens with hydrogen peroxide are preferable.

As hydrogen peroxide used for preparing the oxide of tungsten obtained by reacting at least one tungstens with hydrogen peroxide, an aqueous solution thereof is usually used. The concentration of hydrogen peroxide in the aqueous hydrogen peroxide solution is not particularly limited and it is practically 1 to 60% by weight.

As hydrogen peroxide used for reaction with at least one tungstens, commercially available one may usually be used as it is, and if necessary, one obtained by adjusting the concentration by dilution or concentration may be used.

The amount of hydrogen peroxide used for making react with at least one tungstens is usually 3 moles or more, and preferably 5 moles or more relative to 1 mole of tungstens, and the upper limit thereof is not particularly defined.

The oxide of tungsten is prepared by reacting at least one tungstens with hydrogen peroxide, and the reaction is usually conducted by mixing the both in an aqueous solution. Tungstens may be reacted with hydrogen peroxide in an organic solvent such as an ether solvent such as diethyl ether, methyl tert-butyl ether and tetrahydrofuran, an ester solvent such as ethyl acetate, a tertiary alcohol solvent such as tert-butanol, a nitrile solvent such as acetonitrile and propionitrile, or in a mixed solvent of the organic solvent and water.

The preparing temperature on preparing the oxide of tungsten is usually −10 to 100° C.

A homogeneous solution or suspension containing the oxide of tungsten can be prepared by reacting the tungstens with hydrogen peroxide in water, in the organic solvent or in the mixed solvent of the organic solvent and water. The oxide of tungsten may be isolated from the preparation solution by concentration to use for the reaction of the organic compound and hydrogen peroxide, and the preparation solution containing the oxide of tungsten may be used as it is.

As the organic compound used for the reaction with hydrogen peroxide in the presence of the tungsten catalyst, it is not particularly limited in so far as it can be reacted with hydrogen peroxide. Examples of the organic compound include an olefin compound, an alcohol compound, a nitrogen-containing compound such as an amine compound and a sulfide compound. As the organic compound, commercially available one may be used and one produced according to known methods may be used.

The reaction of the organic compound and hydrogen peroxide is usually conducted according to known methods. When the olefin compound is used as the organic compound, the reaction is conducted according to the method described in, for example, JP 8-291104 A or EP 1188735 B, and an oxidation product or products such as the corresponding epoxide, ketone, aldehyde and carboxylic acid compound are obtained. When the alcohol compound is used as the organic compound, the reaction is conducted according to the method described in, for example, JP 2003-201266 A, JP 2003-96016 A or JP 2004-217625 A, and an oxidation product or products such as the corresponding carboxylic acid compound are obtained. When the nitrogen-containing compound is used as the organic compound, the reaction is conducted according to the method described in, for example, U.S. Pat. No. 4,596, 874, JP 2006-231677 A, JP 2003-231677 A, JP 2003-261516 A, JP 2003-277329 A, JP 2003-277330 or JP 2003-286243 A, and an oxidation product or products such as the corresponding N-oxide, oxime, nitro and nitrone compound are obtained. When the sulfide compound is used as the organic compound, the reaction is conducted according to the method described in, for example, J. Org. Chem., 28, 1140 (1963) or EP 1334956 A, and an oxidation product or products such as the corresponding sulfoxide and sulfone compound are obtained.

The reaction mixture obtained by reacting the organic compound with hydrogen peroxide in the presence of the tungsten catalyst usually contains a oxidation product or products, an unreacted organic compound, by-products, unreacted hydrogen peroxide and the like. The tungsten catalyst used is usually converted to tungstic acid ($WO_3 \cdot H_2O$) by the reaction, and it is dissolved in the reaction mixture or a part thereof is precipitated in the reaction mixture.

The reaction mixture in which tungstic acid is dissolved or a part of tungstic acid is precipitated may be used to the present invention.

The present invention is recovering tungsten contained in the tungsten catalyst used as tungstic acid by blowing a gas into the reaction mixture to precipitate tungstic acid and separating tungstic acid precipitated.

After isolating the desired oxidation product or products by a means such as crystallization from the reaction mixture, the gas may be blown, and the gas may be blown as it is without isolating the oxidation product or products.

As the gas used, it is not particularly limited in so far as it is not reacted with the oxidation product or products or unreacted organic compound in the reaction mixture. Examples of the gas include hydrogen, nitrogen, oxygen, helium, argon and air, and nitrogen and air are preferable.

The amount of the gas blown is usually 1% by volume/minute or more relative to 1 volume of the reaction mixture, and the upper limit is not particularly defined and in the viewpoint of handling, it is preferably 30% by volume/minute or less.

The blowing of the gas is usually conducted in the presence of water. The amount of water to be used is usually 1 part by weight or more relative to 1 part by weight of the tungsten catalyst. The upper limit is not particularly defined.

When the gas is blown, pH of the reaction mixture is usually 0 to 6. Since pH of the reaction mixture differs depending on kinds of the tungsten catalyst used, the gas may be blown into after adjusting pH of the reaction mixture, if necessary, using an acid such as hydrochloric acid, sulfuric acid and nitric acid, or an alkali such as sodium hydroxide.

The temperature of blowing the gas is usually 20 to 130° C., and preferably 50 to 100° C. The blowing is usually conducted under an ordinary pressure condition and may be conducted under pressurized or reduced pressure condition.

The time of blowing the gas is usually 1 to 30 hours and preferably 3 to 20 hours.

Tungstic acid is precipitated by blowing the gas into the reaction mixture, and in order to accelerate the precipitation of tungstic acid, a little amount of tungstic acid may be added to the reaction mixture. The amount of tungstic acid added thereto is usually 0.01 to 0.1% by weight relative to 1 part by weight of the tungsten catalyst used in the reaction.

Tungstic acid precipitated can be usually isolated by filtrating the reaction mixture as it is or, if necessary, after cooling. When the gas is blown into it without isolating the oxidation product or products, the oxidation product or products are also precipitated as crystals in the reaction mixture together with tungstic acid depending on the temperature of blowing the gas. On such case, tungstic acid can be isolated by heating the reaction mixture in which tungstic acid and the oxidation product or products are precipitated to dissolve the oxidation product or products followed by filtrating. Tungstic acid isolated can be used again for the oxidation reaction as it is or, if necessary, after drying. The oxidation product or products can be isolated by concentrating or crystallizing the reaction mixture obtained after isolating tungstic acid, as it is, or, if necessary, after decomposing unreacted hydrogen peroxide by a reducing agent such as sodium sulfite.

EXAMPLES

The present invention will be further illustrated by Examples in detail below, but the present invention is not limited by these Examples. The analysis was conducted by high performance liquid chromatography.

Example 1

A reaction mixture obtained by oxidizing cyclohexane in a liquid phase was washed with water to obtain a reaction mixture containing cyclohexanone and cyclohexanol and a wastewater containing hydroxycaproic acid (content of hydroxycaproic acid: 7.5% by weight). In the wastewater, adipic acid, glutaric acid, ε-caprolactone, esters of adipic acid and esters of hydroxycaproic acid were contained other than hydroxycaproic acid.

Into a 2 L four-necked flask equipped with a reflux condenser, 26 g of sodium tungstate dihydrate, 30 g of water and 68 g of 69% by weight nitric acid were charged to prepare a suspension containing the tungsten catalyst. Into this, 1200 g of the above-mentioned wastewater containing hydroxycaproic acid was charged and the inner temperature was adjusted to 80° C. After adding 248 g of aqueous 30% by weight hydrogen peroxide solution dropwise thereto over 6 hours at the same temperature, the resultant mixture was kept to stir for 2 hour to obtain a reaction mixture containing adipic acid. Into this reaction mixture, nitrogen gas was blown at 150 mL/minute for 24 hours with stirring at an inner temperature of 80° C. to precipitate yellow solids. The reaction mixture was stood at an inner temperature of 70° C. and the supernatant solution was removed by decantation. The residual suspension containing yellow solids was filtrated to separate yellow solids. Yellow solids separated were washed with 20 g of water and 20 g of acetone. The supernatant solution and filtrate obtained were mixed and analyzed to find the yield of adipic acid was 74%.

After drying yellow solids obtained, they were analyzed by powder X-ray diffraction method to find all of them were tungstic acid ($WO_3 \cdot H_2O$) and tungsten oxide ($WO_3$) was not included therein. The obtained amount of tungstic acid: 19.5 g, recover rate of tungsten: 99.0%.

The yield of adipic acid was calculated by the following formula.

$$\text{Yield of adipic acid (\%)} = \frac{\begin{pmatrix} \text{Number of moles of adipic} \\ \text{acid in the supernatant} \\ \text{solution and the filtrate} \end{pmatrix} - \begin{pmatrix} \text{Number of moles of} \\ \text{adipic acid in the} \\ \text{wastewater containing} \\ \text{hydroxycaproic acid} \end{pmatrix}}{\text{Number of moles of adipic acid}} \times 100$$

in the wasterwater containing hydroxycaproic acid

Example 2

Into a 2 L four-necked flask equipped with a reflux condenser, 26 g of sodium tungstate dihydrate, 30 g of water and 68 g of 69% by weight nitric acid were charged to prepare a suspension containing the tungsten catalyst. Into this, 1200 g of the wastewater containing hydroxycaproic acid, which was the same as that used in Example 1, was charged and the inner temperature was adjusted to 80° C. 248 g of aqueous 30% by weight hydrogen peroxide solution was added dropwise thereto over 6 hours at the same temperature and kept to stir for 4 hour to obtain a reaction mixture containing adipic acid. PH of the reaction mixture was 2.1. Into the reaction mixture obtained, hydrogen gas was blown at 150 mL/minute for 12 hours with stirring at an inner temperature of 80° C. to precipitate yellow solids. pH of the reaction mixture at that time was 2.0. The reaction mixture was stood at an inner temperature of 70° C. and the supernatant solution was removed by decantation. The residual suspension containing yellow solids was filtrated to separate yellow solids. Yellow solids separated were washed with 20 g of water and 20 g of acetone. The supernatant solution and filtrate obtained were mixed and analyzed to find the yield of adipic acid was 70%. The yield of adipic acid was calculated by the formula described in the above-mentioned Example 1.

After drying yellow solids obtained, they were analyzed by powder X-ray diffraction method to find all of them were tungstic acid and tungsten oxide was not included therein. The obtained amount of tungstic acid: 19.3 g, recover rate of tungsten: 98.0%.

Example 3

Into a 2 L four-necked flask equipped with a reflux condenser, 9.9 g of tungstic acid recovered in Example 1, 9.8 g of tungstic acid recovered in Example 2, 30 g of water and 58 g of 69% by weight nitric acid were charged to prepare a suspension containing the tungsten catalyst. Into this, 1200 g of the wastewater containing hydroxycaproic acid, which was the same as that used in Example 1, was charged and the inner temperature was adjusted to 80° C. 271 g of aqueous 30% by weight hydrogen peroxide solution was added dropwise thereto over 6 hours at the same temperature and kept to stir for 4 hour to obtain a reaction mixture containing adipic acid. Into the reaction mixture obtained, nitrogen gas was blown at 150 mL/minute for 8 hours with stirring at an inner temperature of 80° C. to precipitate yellow solids. The reaction mixture was stood at an inner temperature of 70° C. and the supernatant solution was removed by decantation. The residual suspension containing yellow solids was filtrated to separate yellow solids. Yellow solids separated were washed with 20 g of water and 20 g of acetone. The supernatant solution and filtrate obtained were mixed and analyzed to find the yield of adipic acid was 75%. The yield of adipic acid was calculated by the formula described in the above-mentioned Example 1.

After drying yellow solids obtained, they were analyzed by powder X-ray diffraction method to find all of them were tungstic acid and tungsten oxide was not included therein. The obtained amount of tungstic acid: 19.6 g, recover rate of tungsten: 99.5%.

Comparative Example 1

Into a 2 L four-necked flask equipped with a reflux condenser, 26 g of sodium tungstate dihydrate, 30 g of water and 68 g of 69% by weight nitric acid were charged to prepare a suspension containing the tungsten catalyst. Into this, 1200 g of the wastewater containing hydroxycaproic acid, which was the same as that used in Example 1, was charged and the inner temperature was adjusted to 80° C. After adding 271 g of aqueous 30% by weight hydrogen peroxide solution dropwise thereto over 6 hours at the same temperature, the resultant mixture was kept to stir for 4 hour to obtain a reaction mixture containing adipic acid. The reaction mixture obtained was further kept for 24 hours with stirring at an inner temperature of 80° C. The reaction mixture was stood at an inner temperature of 70° C. and the supernatant solution was removed by decantation. The residual suspension containing yellow solids was filtrated to separate pale yellow solids. Pale yellow solids separated were washed with 20 g of water and 20 g of acetone. The supernatant solution and filtrate obtained were mixed and analyzed to find the yield of adipic acid was 82%. The yield of adipic acid was calculated based on the formula described in the above-mentioned Example 1.

After drying pale yellow solids obtained, they were analyzed by powder X-ray diffraction method to find 66% by weight thereof was tungstic acid and 34% by weight thereof was tungsten oxide.

The obtained amount of pale yellow solids: 15.0 g
Recover rate of tungsten:
50.3% as tungstic acid
27.9% as tungsten oxide Example 4

Into a 500 mL four-necked flask equipped with a reflux condenser, 3.0 g of sodium tungstate dihydrate, 350 g of water and 5.0 g of 98% by weight sulfuric acid were charged to prepare a suspension containing the tungsten catalyst. The suspension of the tungsten catalyst was heated at an inner temperature of 90° C., and 100 g of tetrahydrophthalic anhydride was added thereto by a small amount. After adding 188.1 g of aqueous 60% by weight hydrogen peroxide solution dropwise thereto over 3 hours at the same temperature, the resultant mixture was kept for 5 hours to obtain a reaction mixture containing 1,2,3,4-butanetetracarboxylic acid. Into the reaction mixture obtained, nitrogen gas was blown at 100 mL/minute for 24 hours with stirring at an inner temperature of 80° C. to precipitate yellow solids. The reaction mixture was stood at an inner temperature of 60° C. and the supernatant solution was removed by decantation. The residual suspension containing yellow solids was filtrated to separate yellow solids. Yellow solids separated were washed with 10 g of water and 10 g of acetone. The supernatant solution and filtrate obtained were mixed and analyzed to find the yield of 1,2,3,4-butanetetracarboxylic acid was 85.2%.

After drying yellow solids obtained, they were analyzed by powder X-ray diffraction method to find all of them were tungstic acid and tungsten oxide was not included therein. The obtained amount of tungstic acid: 2.26 g, recover rate of tungsten: 99.6%.

Comparative Example 2

According to the same manner as that described in Example 4, 980 mg of pale yellow powders containing tungstic acid and tungsten oxide was recovered except that nitrogen gas was not blown.

Example 5

A reaction mixture obtained by oxidizing cyclohexane in a liquid phase was washed with water to obtain a reaction mixture containing cyclohexanone and cyclohexanol and a wastewater containing hydroxycaproic acid (content of hydroxycaproic acid: 7.5% by weight). In the wastewater, adipic acid, glutaric acid, ε-caprolactone, esters of adipic acid and esters of hydroxycaproic acid were contained other than hydroxycaproic acid.

Into a 2 L four-necked flask equipped with a reflux condenser, 26.1 g of sodium tungstate dihydrate, 100 g of water and 78.2 g of 60% by weight nitric acid were charged to prepare a suspension containing the tungsten catalyst. Into this, 1200 g of the above-mentioned wastewater containing hydroxycaproic acid was charged and the inner temperature was adjusted to 80° C. After adding 270.4 g of aqueous 30% by weight hydrogen peroxide solution dropwise thereto over 6 hours at the same temperature, the resultant mixture was kept to stir for 2 hour to obtain a reaction mixture containing adipic acid. Into this reaction mixture, nitrogen gas was blown at 150 mL/minute for 12 hours with stirring at an inner temperature of 80° C. to precipitate yellow solids. The reaction mixture was stood at an inner temperature of 70° C. and the supernatant solution was removed by decantation. The residual suspension containing yellow solids was filtrated to separate yellow solids. Yellow solids separated were washed with 20 g of water and 20 g of acetone. The supernatant solution and filtrate obtained were mixed and analyzed to find the yield of adipic acid was 33%. The yield of adipic acid was calculated based on the formula described in the above-mentioned Example 1.

The obtained amount of tungstic acid: 18.8 g, recover rate of tungsten: 95.4%.

Example 6

Into a 2 L four-necked flask equipped with a reflux condenser, 22.5 g of sodium tungstate dihydrate, 100 g of water and 78.2 g of 60% by weight nitric acid were charged to prepare a suspension containing the tungsten catalyst. Into this, 1200 g of the wastewater containing hydroxycaproic acid, which was the same as that used in Example 5, was charged and the inner temperature was adjusted to 80° C. After adding 270.4 g of aqueous 30% by weight hydrogen peroxide solution dropwise thereto over 6 hours at the same temperature, the resultant mixture was kept to stir for 2 hour to obtain a reaction mixture containing adipic acid. Into this reaction mixture, air was blown at 150 mL/min. for 12 hours with stirring at an inner temperature of 80° C. to precipitate yellow solids of tungstic acid. The reaction mixture was stood at an inner temperature of 70° C. and the supernatant solution was removed by decantation. The residual suspension containing yellow solids was filtrated to separate yellow solids. Yellow solids separated were washed with 20 g of water and 20 g of acetone. The supernatant solution and filtrate obtained were mixed and analyzed to find the yield of adipic acid was 36%. The yield of adipic acid was calculated based on the formula described in the above-mentioned Example 1.

The obtained amount of tungstic acid: 16.2 g, recover rate of tungsten: 95.2%.

INDUSTRIAL APPLICABILITY

According to the present invention, tungsten included in the tungsten catalyst used can be recovered as tungstic acid ($WO_3.H_2O$) in a good yield. Tungstic acid recovered can be used again for the oxidation reaction and tungsten source can be used efficiently and therefore, it is an industrially useful method.

The invention claimed is:

1. A method for recovering tungsten from a reaction mixture obtained by reacting an organic compound with hydrogen peroxide in the presence of a tungsten catalyst, the method comprising blowing a gas into the reaction mixture to precipitate tungstic acid ($WO_3H_2O$) and separating the precipitated tungstic acid, wherein the gas is non-reactive with the reaction mixture.

2. The method for recovering tungsten according to claim 1, wherein a pH of the reaction mixture is in a range of 0 to 6.

3. The method for recovering tungsten according to claim 1, wherein the gas is nitrogen or air.

4. The method for recovering tungsten according to claim 1, wherein a temperature of blowing the gas is 20 to 130° C.

5. The method for recovering tungsten according to claim 1, wherein a time of blowing the gas is 1 to 30 hours.

6. The method for recovering tungsten according to claim 1, wherein the tungsten catalyst is selected from the group consisting of tungsten metal, tungsten boride, tungsten carbide, tungsten sulfide, tungsten oxide, tungstic acid and a salt of tungstic acid.

7. The method for recovering tungsten according to claim 1, wherein the tungsten catalyst is an oxide of tungsten obtained by reacting at least one tungsten material selected from the group consisting of tungsten metal, tungsten boride, tungsten carbide, tungsten sulfide, tungsten oxide, tungstic acid and a salt of tungstic acid with hydrogen peroxide.

* * * * *